United States Patent
Ganta et al.

(10) Patent No.: US 8,084,619 B2
(45) Date of Patent: *Dec. 27, 2011

(54) GAS GENERANT COMPOSITIONS

(75) Inventors: Sudhakar R. Ganta, Troy, MI (US);
Graylon K. Williams, Warren, MI (US);
Cory G. Miller, Rochester, MI (US)

(73) Assignee: TK Holdings, Inc., Armada, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/916,742

(22) Filed: Nov. 1, 2010

(65) Prior Publication Data

US 2011/0046390 A1 Feb. 24, 2011

Related U.S. Application Data

(62) Division of application No. 11/800,923, filed on May 7, 2007, now Pat. No. 7,847,102.

(51) Int. Cl.
*C07D 257/06* (2006.01)
*C06B 43/00* (2006.01)
(52) U.S. Cl. ...................... 548/251; 149/109.2
(58) Field of Classification Search ............ 548/251; 149/109.2
See application file for complete search history.

(56) References Cited

U.S. PATENT DOCUMENTS

| 7,692,024 B2 | 4/2010 | Ganta et al. | 548/250 |
| 7,847,102 B2 | 12/2010 | Ganta et al. | 548/251 |

OTHER PUBLICATIONS

Office Action U.S. Appl. No. 11/800,924, filed May 7, 2007, Mailed Mar. 5, 2010 (183).
Office Action U.S. Appl. No. 11/800,918, filed May 7, 2007, Mailed Sep. 21, 2010 (184).
Office Action U.S. Appl. No. 11/906,345, filed Oct. 1, 2007, Mailed Sep. 23, 2010(165).
Office Action U.S. Appl. No. 11/800,922, filed May 7, 2007, Mailed Sep. 22, 2010 (182).
Office Action U.S. Appl. No. 11/800,922, filed May 7, 2007, Mailed Jan. 14, 2011 (00182).

*Primary Examiner* — Robert Havlin
(74) *Attorney, Agent, or Firm* — L. C. Begin & Associates, PLLC

(57) ABSTRACT

A novel compound, used for example, as a gas generating fuel, is defined as a compound having the structural formula of $R_3$—$R_1$—$R_2$, wherein R1 is a urea group, R2 is a tetrazolyl group with a C—N bond to the urea group, and R3 may be defined as a non-tetrazolyl, triazolyl, heterocyclic, heterocyclic amine, aliphatic, aliphatic amine, aryl, alkyl, hydrogen, or nitrogen group linked to the free nitrogen on the urea group. A method of making the compound is also provided. A gas generating composition 12 containing the novel compound as a fuel, and an oxidizer is also provided. The novel compound may be contained within a gas generant composition 12, within a gas generator 10. The gas generator 10 may be contained within a gas generating system such as an airbag inflator 10 or seat belt assembly 150, or more broadly within a vehicle occupant protection system 180.

5 Claims, 1 Drawing Sheet

GAS GENERANT COMPOSITIONS

CROSS-REFERENCE TO RELATED APPLICATIONS

This application claims the benefit of and is a divisional application of prior co-owned U.S. Utility application Ser. No. 11/800,923 filed on May 7, 2007, now U.S. Pat. No. 7,847,102.

TECHNICAL FIELD

The present invention relates generally to gas generating systems, and to gas generating compositions employed in gas generator devices for automotive restraint systems, for example.

BACKGROUND OF THE INVENTION

The present invention relates to gas generant compositions that upon combustion produce a relatively smaller amount of solids and a relatively abundant amount of gas. It is an ongoing challenge to reduce the amount of solids and increase the amount of gas thereby decreasing the filtration requirements for an inflator. As a result, the filter may be either reduced in size or eliminated altogether thereby reducing the weight and/or size of the inflator. Additionally, reduction of combustion solids provides relatively greater amounts of gaseous products per gram or unit of gas generating composition. Accordingly, less gas generant is required when greater mols of gas are produced per gram of gas generant. The result is typically a smaller and less expensive inflator due to reduced manufacturing complexity.

Yet another concern is that the compositions must exhibit burn rates that are satisfactory with regard to use in vehicle occupant protection systems. In particular, compositions containing phase stabilized ammonium nitrate may exhibit relatively lower burn rates requiring various measures to improve the burn rate. Accordingly, the development of energetic fuels is one ongoing research emphasis whereby the less aggressive burn characteristics of preferred oxidizers such as phase stabilized ammonium nitrate are accommodated and compensated.

SUMMARY OF THE INVENTION

The above-referenced concerns are resolved by gas generators or gas generating systems containing novel fuel constituents within novel gas generant compositions. Novel fuel constituents or compounds may be defined as a molecule having the structural formula of $R_3$—$R_1$—$R_2$, wherein R1 is a urea group, R2 is a tetrazolyl group with a C—N bond to the urea group, and R3 may be defined as a C-tetrazolyl, N-tetrazolyl, triazolyl, heterocyclic-triazines, heterocyclic amine, aliphatic, aliphatic amine, aromatic, aromatic amines, aryl, alkyl, alkenyl, alkynyl, hydrogen, or nitramine group linked to the tree nitrogen on the urea group. R3 is preferably a tetrazolyl or triazolyl group with a C—N bond to the urea group. It will be appreciated that the novel compounds formed in accordance with the present invention may have applications other than as gas generant constituents.

An optional second fuel may be selected from tetrazoles and salts thereof, triazoles and salts thereof, azoles and salts thereof, guanidines and salts thereof, guanidine derivatives, amides, and mixtures thereof. An oxidizer is selected from metal and nonmetal nitrates, nitrites, chlorates, perchlorates, oxides, other known oxidizers, and mixtures thereof.

In further accordance with the present invention, a gas generator or gas generating system, and a vehicle occupant protection system incorporating the gas generant composition are also included.

DETAILED DESCRIPTION OF THE INVENTION

Figure 1:
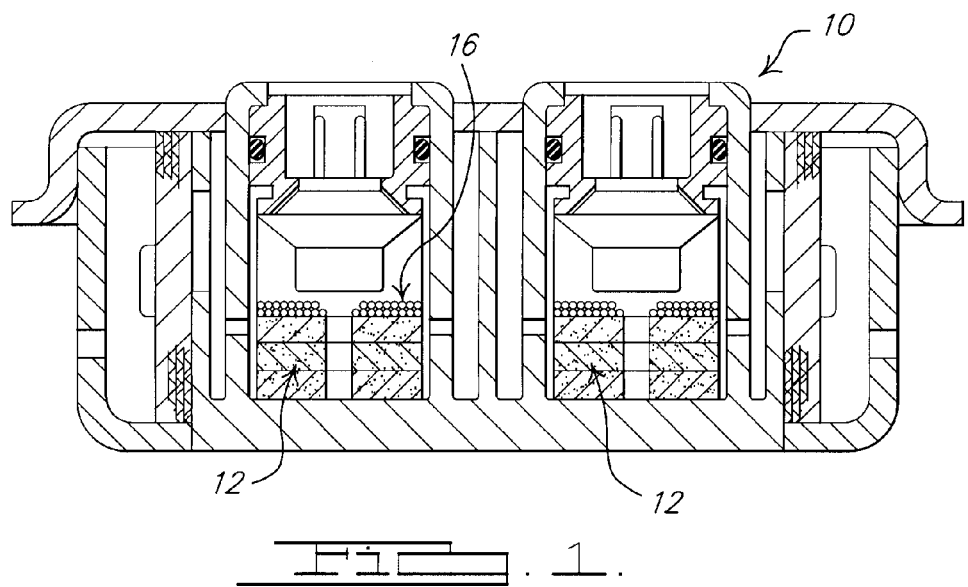
FIG. 1 is a cross-sectional side view showing the general structure of an inflator in accordance with the present invention.

A first aspect of the present invention provides a novel method of forming a nitrogen-containing compound, useful as a fuel within a gas generant system, for example. The method may be described by the following steps:

1. Providing a solution of 5-amino tetrazole and triethyl amine in acetonitrile, wherein 5-amino tetrazole and triethyl amine are provided in roughly equimolar amounts, and acetonitrile is provided in an amount sufficient to solublize the reactants of this method. When dissolved in acetonitrile, the mixture becomes a clear solution.
2. Adding triphosgene in about 0.3 to 0.4 of the molar amount of triethyl amine, to a cooled solution, at about 0 -10 C degrees Celsius.
3. Stirring the mixture, slowly bringing it to room temperature.
4. Continue stirring, for about four hours, to form the reaction intermediate, tetrazole isocyanate, as may be determined by IR spectroscopy.
5. Adding one equivalent of 5-aminotetrazole/triethylamine.
6. Heating to temperatures greater than room temperature, from room temperature to about 80 degrees Celsius.
7. Continually stirring to permit reaction for a sufficient period of time to result in the formation of the urea derivative, as confirmed by IR spectroscopy, that is 1720, 1654 cm–1 for urea, and 3200 cm–1 for N—H stretching.
8. Cooling the solution to room temperature and bubbling nitrogen gas therethrough for about 10-30 minutes to sufficiently react and eliminate any unreacted phosgene gas.
9. Removing the remaining solvent, preferably under vacuum conditions
10. Washing the solid with water.
11. Drying the solid.

Reactions I and II as given below illustrate the formation of two varieties of a fuel in accordance with the present invention. The following exemplifies, and provides a blueprint for, reactions in accordance with the present invention.

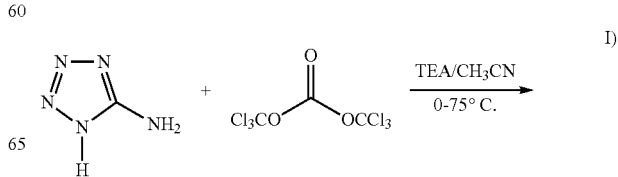

I)

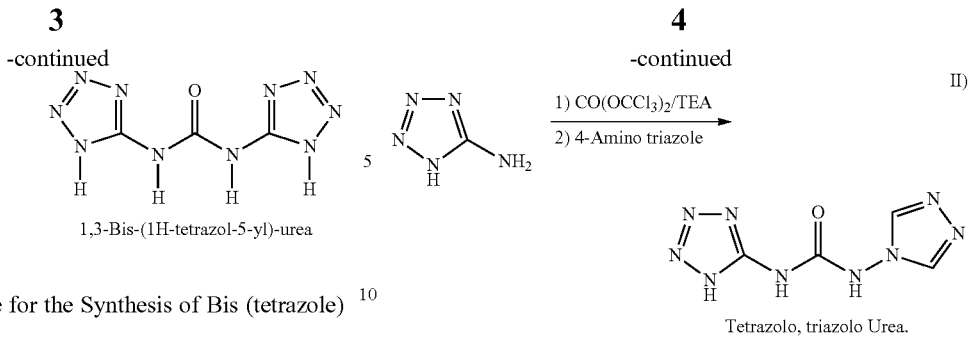

1,3-Bis-(1H-tetrazol-5-yl)-urea

Experimental Procedure for the Synthesis of Bis (tetrazole) Urea:

5-Amino tetrazole (5 g, 58.7820 mmol) was dissolved in dry acetonitrile (75 mL). Triethylamine (8.24 mL, 59.3692 mmol) was then added and the mixture was stirred at room temperature for 5 minutes. The mixture was then cooled to 0° C. Triphosgene (6.454 g, 21.7493 mmol) was then slowly added over a period of 20 minutes. The solution was then stirred at room temperature for about four hours.

The formation of tetrazole isocyanate, an intermediate, was monitored by infrared spectroscopy at 2170 cm−1. Next, one equivalent of 5-amino tetrazole/triethylamine was added to the solution, and the mixture was then heated to 75° C. The solution was then reacted overnight, until the formation of urea derivative was observed by infrared spectroscopy (1720, 1654 cm−1 for urea and 3200 cm−1 for N—H stretching).

The reaction was then brought to room temperature and nitrogen gas was bubbled therethrough for about 20 minutes to eliminate any unreacted phosgene gas. A white solid compound resulted. The solvent was removed under reduced pressure and the resultant solid was washed with water (2×200 mL) and dried in an oven at 105° C. for overnight to yield in 75% of BTU.

BTU was re-crystalized from boiling water, the pure BTU decomposes at 268° C. with a relatively large exotherm. This synthetic methodology can be extended to make various other urea derivatives.

Theoretical Calculation:

With a fuel/oxidizer ratio of 28/72, that is BTU/PSAN in wt %, then the propellant oxygen balance equals −0.19. This oxygen balance results in a 96.6% gas yield and produces 4.03 moles of gas per 100 gm of propellant.

Accordingly, a general synthetic strategy for many urea derivatives may be defined by the following reaction;

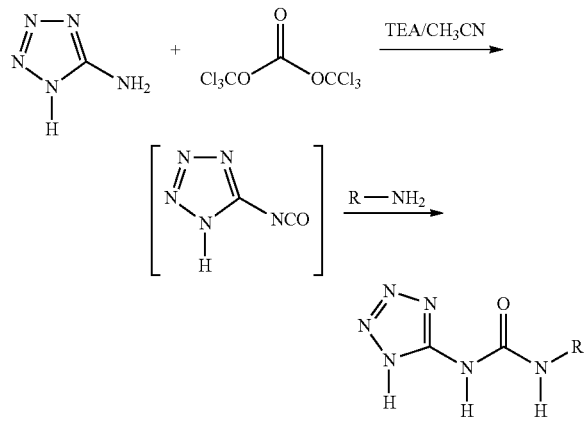

R = alkyl, aryl, heterocyles.

Tetrazolo, triazolo Urea.

Experimental Procedure for the Synthesis of 1-triazolyl-3-tetrazolyl Urea:

5-Amino tetrazole (10 g, 17.56 mmol) was dissolved in acetonitrile (150 mL). Triethylamine (17.95 mL, 129.316 mmol) was then added and the mixture was stirred at room temperature for 5 minutes. The mixture was then cooled to 0° C. Triphosgene (12.9 g, 43.4987 mmol) was then slowly added over a period of 20 minutes. The solution was then stirred at room temperature for about four hours.

The formation of tetrazole isocyanate, an intermediate, was monitored by infrared spectroscopy at 2170 cm−1. To this mixture one equivalent of 4-amino triazole (9.983 g, 118.7356 mmol)/triethylamine (17.95 ml, 129.316 mmol) was then added, and the mixture heated to 75° C. for 4 hrs, until the formation of urea derivative was observed by infrared spectroscopy (1730, 1599 cm−1 for urea and 3198, 3140 cm−1 for N—H stretching).

The reaction was then brought to room temperature and nitrogen gas was bubbled therethrough for about 20 minutes to eliminate any unreacted phosgene gas. A white solid compound resulted. The solvent was removed under reduced pressure and the resultant solid was washed with water (2×200 mL) and dried in an oven at 105° C. for overnight to yield 15 g or 60% pure tetrazolo, triazolo urea (TTU). The TTU was tested to show that the reaction product decomposed at 250° C. with a large exotherm.

Infrared (IR) evaluations indicate 1730, 1599 cm−1 for urea, 3198, 3140 cm−1 for N—H stretching, thereby confirming the reaction product structure. Differential scanning calorimeter (DSC) evaluations, showing relatively high energy, indicate a sharp exotherm at 250° C.

As shown in the reactions, each fuel is nitrogen-rich, thereby maximizing the non-metal constituents of the total gas generant composition. The reaction product exhibited relatively high energy and when combined with oxidizers as described below, also exhibited good burn rates in excess of 0.4 inches per second, when evaluated as known in the art.

Theoretical Calculation:

With a fuel/oxidizer ratio of 22/78, that is TTU/PSAN in wt %, then the propellant oxygen balance equals −0.02. This oxygen balance results in a 96.6% gas yield and produces 4.05 moles of gas per 100 gm of propellant.

Accordingly, the present invention includes gas generant compositions containing a high-energy, nitrogen-rich fuel defined as a compound having the structural formula of $R_3$—$R_1$—$R_2$, wherein R1 is a urea group, R2 is a tetrazolyl group with a C—N bond to the urea group, and R3 may be defined as a C-tetrazolyl, N-tetrazolyl, triazolyl, heterocyclic-triazines, heterocyclic amine, aliphatic, aliphatic amine, aromatic, aromatic amines, aryl, alkyl, alkenyl, alkynyl, hydrogen, or nitramine group linked to the free nitrogen on the urea group. R3 is preferably a tetrazolyl or triazolyl group with a C—N bond to the urea group.

The fuel is provided at about 5-50 wt % and more preferably at about 15-30 wt %, of the gas generant composition.

Optional secondary fuels include tetrazoles such as 5-aminotetrazole; metal salts of azoles such as potassium 5-aminotetrazole; nonmetal salts of azoles such as diammonium salt of 5,5'-bis-1H-tetrazole: nitrate salts of azoles such as 5-aminotetrazole; nitramine derivatives of azoles such as 5-aminotetrazole; metal salts of nitramine derivatives of azoles such as dipotassium 5-aminotetrazole; metal salts of nitramine derivatives of azoles such as dipotassium 5-aminotetrazole; nonmetal salts of nitramine derivatives of azoles such as monoammonium 5-aminotetrazole and; guanidiness such as dicyandiamide; salts of guanidines such as guanidine nitrate; nitro derivatives of guanidines such as nitroguanidine; azoamides such as azodicarbonamide; nitrate salts of azoamides such as azodicarbonamidine dinitrate; and mixtures thereof. The secondary fuel can be used within this system as co-fuels to the primary fuel. If used, the secondary fuel when combined with the primary fuel constitutes about 5-50 wt % of the gas generant composition. By itself, the secondary fuel constitutes 0-45 wt %, and more preferably about 15-30 wt % when used.

An oxidizer component is selected from at least one exemplary oxidizer selected from basic metal nitrates, and, metal and nonmetal nitrates, chlorates, perchlorates, nitrites, oxides, and peroxides such as basic copper (II) nitrate, strontium nitrate, potassium nitrate, potassium nitrite, iron oxide, and copper oxide. Other oxidizers as recognized by one of ordinary skill in the art may also be employed. The oxidizer is generally provided at about 50-95 wt % of the gas generant composition.

Processing aids such as fumed silica, boron nitride, and graphite may also be employed. Accordingly, the gas generant may be safely compressed into tablets, or slugged and then granulated. The processing aid is generally provided at about 0-15 wt %, and more preferably at about 0-5 wt %.

Slag formers may also be provided and are selected from silicon compounds such as elemental silicone; silicon dioxide; silicones such as polydimethylsiloxane; silicates such as potassium silicates; natural minerals such as talc and clay, and other known slag formers. The slag former is typically provided at about 0-10 wt %, and more preferably at about 0-5 wt %.

The compositions of the present invention are formed from constituents as provided by known suppliers such as Aldrich or Fisher Chemical companies. The compositions may be provided in granulated form and dry-mixed and compacted in a known manner, or otherwise mixed as known in the art. The compositions may be employed in gas generators typically found in airbag devices or occupant protection systems, or in safety belt devices, or in gas generating systems such as a vehicle occupant protection system, all manufactured as known in the art, or as appreciated by one of ordinary skill.

As shown in FIG. 1, an exemplary inflator or gas generating system 10 incorporates a dual chamber design to tailor containing a primary gas generating composition 12 formed as described herein, may be manufactured as known in the art. U.S. Pat. Nos. 6,422,601, 6,805,377, 6,659,500, 6,749,219, and 6,752,421 exemplify typical airbag inflator designs and are each incorporated herein by reference in their entirety.

Figure 2:
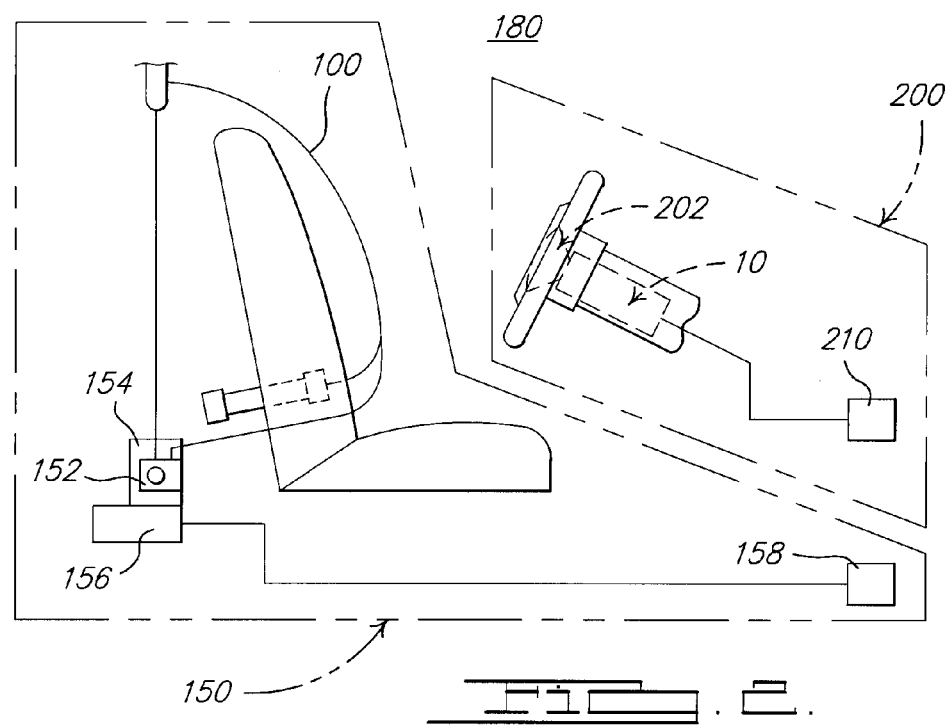
FIG. 2 is a schematic representation of an exemplary vehicle occupant restraint system containing a gas generant composition in accordance with the present invention.

Referring now to FIG. 2, the exemplary inflator or gas generating system 10 described above may also be incorporated into an airbag system 200. Airbag system 200 includes at least one airbag 202 and an inflator 10 containing a gas generant composition 12 in accordance with the present invention, coupled to airbag 202 so as to enable fluid communication with an interior of the airbag. Airbag system 200 may also include (or be in communication with) a crash event sensor 210. Crash event sensor 210 includes a known crash sensor algorithm that signals actuation of airbag system 200 via, for example, activation of airbag inflator 10 in the event of a collision.

Referring again to FIG. 2, airbag system 200 may also be incorporated into a broader, more comprehensive vehicle occupant restraint system 180 including additional elements such as a safety belt assembly 150. FIG. 2 shows a schematic diagram of one exemplary embodiment of such a restraint system. Safety belt assembly 150 includes a safety belt housing 152 and a safety belt 100 extending from housing 152. A safety belt retractor mechanism 154 (for example, a spring-loaded mechanism) may be coupled to an end portion of the belt. In addition, a safety belt pretensioner 156 containing gas generating/auto ignition composition 12 may be coupled to belt retractor mechanism 154 to actuate the retractor mechanism in the event of a collision. Typical seat belt retractor mechanisms which may be used in conjunction with the safety belt embodiments of the present invention are described in U.S. Pat. Nos. 5,743,480, 5,553,803, 5,667,161, 5,451,008, 4,558,832 and 4,597,546, incorporated herein by reference. Illustrative examples of typical pretensioners with which the safety belt embodiments of the present invention may be combined are described in U.S. Pat. Nos. 6,505,790 and 6,419,177, incorporated herein by reference.

Safety belt assembly 150 may also include (or be in communication with) a crash event sensor 158 (for example, an inertia sensor or an accelerometer) including a known crash sensor algorithm that signals actuation of belt pretensioner 156 via, for example, activation of a pyrotechnic igniter (not shown) incorporated into the pretensioner. U.S. Pat. Nos. 6,505,790 and 6,419,177, previously incorporated herein by reference, provide illustrative examples of pretensioners actuated in such a manner.

It should be appreciated that safety belt assembly 150, airbag system 200, and more broadly, vehicle occupant protection system 180 exemplify but do not limit gas generating systems contemplated in accordance with the present invention.

It should further be understood that the preceding is merely a detailed description of various embodiments of this invention and that numerous changes to the disclosed embodiments can be made in accordance with the disclosure herein without departing from the scope of the invention. The preceding description, therefore, is not meant to limit the scope of the invention. Rather, the scope of the invention is to be determined only by the appended claims and their equivalents.

What is claimed is:

1. A method of forming a compound comprising the steps of:
   providing a solution of 5-amino tetrazole and triethyl amine in acetonitrile, wherein 5-amino tetrazole and triethyl amine are provided in roughly equimolar amounts, and acetonitrile is provided in an amount sufficient to solubilize the reactants of this method;
   adding triphosgene in about 0.3 to 0.4 of the molar amount of the methyl amine, to a solution cooled to 0-10 degrees Celsius;
   stirring the mixture to form the reaction intermediate, tetrazole isocyanate;
   adding one equivalent of 5-aminotetrazole/triethylamine;
   heating to temperatures greater than room temperature, from room temperature to about 80 degrees Celsius;
   stirring to permit reaction for a sufficient period of time to result in the formation of the compound, wherein said compound has the structural formula of R$_3$—R$_1$—R$_2$ wherein R1 is a urea group, R2 is a tetrazolyl group with a C—N bond to the urea group, and R3 is an N-tetrazoylyl, triazolyl, heterocyclic-triazine, heterocyclic amine, aromatic amine, alkenyl, alkynyl, or nitramine group linked to the free nitrogen on the urea group.

2. The compound formed by the method of claim 1.

3. A gas generant composition containing the compound of claim 2.

4. A gas generating system containing the compound of claim 2.

5. A vehicle occupant protection system containing the compound of claim 2.

* * * * *

UNITED STATES PATENT AND TRADEMARK OFFICE
CERTIFICATE OF CORRECTION

| | | |
|---|---|---|
| PATENT NO. | : 8,084,619 B2 | Page 1 of 1 |
| APPLICATION NO. | : 12/916742 | |
| DATED | : December 27, 2011 | |
| INVENTOR(S) | : Ganta et al. | |

It is certified that error appears in the above-identified patent and that said Letters Patent is hereby corrected as shown below:

| | |
|---|---|
| Col. 1, line 56 | Delete "tree" and insert -- free -- |
| Col. 4, line 16 | Delete "17.56" and insert -- 117.56 -- |
| Col. 6, line 59, Claim 1 | Delete "methyl" and insert -- triethyl -- |
| Col. 7, line 4, Claim 1 | Delete "tetrazoylyl" and insert -- tetrazolyl -- |

Signed and Sealed this
Twenty-seventh Day of March, 2012

David J. Kappos
*Director of the United States Patent and Trademark Office*